United States Patent
Perello Bestard et al.

(10) Patent No.: US 9,364,490 B2
(45) Date of Patent: Jun. 14, 2016

(54) USE OF DERIVATIVES CONTAINING C—O—P BONDS IN PATIENTS WITH KIDNEY FAILURE

(71) Applicant: LABORATORIS SANIFIT, S.L., Palma de Mallorca (ES)

(72) Inventors: Joan Perello Bestard, Palma de Mallorca (ES); Carolina Salcedo Roca, Palma de Mallorca (ES); Miguel David Ferrer Reynes, Palma de Mallorca (ES); Bernat Isern Amengual, Palma de Mallorca (ES); Pieter H. Joubert, Palma de Mallorca (ES)

(73) Assignee: LABORATORIS SANIFIT, S.L., Palma De Mallorca (ES)

( * ) Notice: Subject to any disclaimer, the term of this patent is extended or adjusted under 35 U.S.C. 154(b) by 0 days.

(21) Appl. No.: 14/212,286

(22) Filed: Mar. 14, 2014

(65) Prior Publication Data
US 2014/0271915 A1 Sep. 18, 2014

Related U.S. Application Data

(60) Provisional application No. 61/791,090, filed on Mar. 15, 2013.

(51) Int. Cl.
*A61K 31/66* (2006.01)
*A61K 45/06* (2006.01)
*A61K 31/6615* (2006.01)

(52) U.S. Cl.
CPC ............ *A61K 31/6615* (2013.01); *A61K 45/06* (2013.01)

(58) Field of Classification Search
CPC ..................... A61K 31/6615; A61K 45/06
See application file for complete search history.

(56) References Cited

U.S. PATENT DOCUMENTS

| 8,277,909 | B2 * | 10/2012 | Simpson | B41M 5/504 428/32.13 |
| 8,377,909 | B2 * | 2/2013 | Freixedas | A61K 31/6615 514/102 |
| 8,778,912 | B2 * | 7/2014 | Freixedas | A61K 9/0026 514/89 |

FOREIGN PATENT DOCUMENTS

WO 2013050603 A1 4/2013

OTHER PUBLICATIONS

"Prevention", Merriam-Webster Online Dictionary [online], [retrieved Feb. 7, 2015] Retrieved from the Internet: <URL: http://www.merriam-webster.com/dictionary/prevention>.*
"Kidney Stones and Chronic Kidney Disease", DaVita [online], [retrieved Nov. 5, 2015] Retrieved from the Internet: <URL: http://www.davita.com/kidney-disease/overview/symptoms-and-diagnosis/kidney-stones-a>.*
O'Neill et al., Treatment with pyrophosphate inhibits uremic vascular calcification; 2011; Kidney International, 79:512-517.*

(Continued)

*Primary Examiner* — Jane C Oswecki
(74) *Attorney, Agent, or Firm* — Sterne, Kessler, Goldstein & Fox P.L.L.C.

(57) ABSTRACT

Use of a derivative containing C—O—P bonds in a controlled release form to treat patients with kidney failure. Moreover, it comprises the use of said derivatives together with other active substances, which particularly may be selected from a list comprising a calcimimetic, vitamin, phosphate binder, thiosulfate, bisphosphonate, pyrophosphate, citrate, diuretic, antihypertensive and anticholesteraemic agent.

11 Claims, 9 Drawing Sheets

(56) References Cited

OTHER PUBLICATIONS

Felix Grases et al., Phytate acts as an inhibitor in formation of renal calculi; Jan. 1, 2007; Frontiers in Bioscience, 12:2580-2587.*

"Prevention", Merriam-Webster Online Dictionary [online], [retrieved Feb. 7, 2015] Retrieved from the Internet: <URL: http:llwww.merriam-webster.com/dictionary/prevention>.*

Bernd Hoppe, "An update on primary hyperoxaluria"; 2012; Nature Reviews Nephrology, 8(8):467-475 (Abstract only).*

Grases et al., "Phytate acts as an inhibitor in formation of renal calculi,"; 2007; Frontiers in Bioscience, 12:2580-2587.*

O'Neill et al., "Treatment with pyrophosphate inhibits uremic vascular calcification," 2011; Kidney International, 79:512-517.*

D. Russo. Progression of coronary artery calcification and cardiac events in patients with chronic renal disease not receiving dialysis, 2011 International Society of Nephrology, Kidney International (2011) 80, pp. 112-118.

R. Shantouf. Total and Individual Coronary Artery Calcium Scores as Independent Predictors of Mortality in Hemodialysis Patients, American Journal of Nephrology, 2010, 31, pp. 419-425.

F. Grases. Phytate acts as an inhibitor in formation of renal calculi, Frontiers in Bioscience 12, pp. 2580-2587, Jan. 1, 2007.

* cited by examiner

USE OF DERIVATIVES CONTAINING C—O—P BONDS IN PATIENTS WITH KIDNEY FAILURE

PRIORITY STATEMENT

This application is a non-provisional patent application claiming priority to U.S. provisional patent application 61/791,090, filed on Mar. 15, 2013, the entirety of which is incorporated by reference.

DESCRIPTION

The present invention relates to the use of a compound comprising C—O—P bonds, in a prolonged release form, to treat diseases in patients with kidney failure, whether undergoing other treatments or not.

PRIOR STATE OF THE ART

Kidney failure (also known as renal impairment or kidney disease) is a disease that causes a progressive loss of kidney function, with a concomitant decrease in the glomerular filtration rate (GFR) or index. Although the initial stages of kidney damage may be asymptomatic, uraemia presents as the disease progresses. Uraemia is a concept that describes the contamination of blood due to incorrect filtration and elimination of toxins by the kidneys.

Kidney disease can be classified as.

Acute kidney injury: a progressive loss of kidney function, which generally causes oliguria and a fluid and electrolyte imbalance. Treatment by dialysis may be necessary until the causes of the disease can be identified and treated.

Chronic kidney disease (CKD): a much slower loss of kidney function over a period of months or years. Depending on the degree of kidney function, five stages of CKD are defined on the basis of the GFR:
Stage 1: normal or high GFR (>90 ml/min)
Stage 2: Mild CKD. GFR=60-89 mi/min
Stage 3: Moderate CKD. GFR=30-59 m/min
Stage 4: Severe CKD. GFR=15-29 ml/min
Stage 5: Terminal CKD. GFR<15 ml/min. Dialysis or a kidney transplant are required to maintain the state of health.

Moreover, it is possible that acute renal failure may occur concomitantly with CKD, which is known as acute-on-chronic renal failure.

Patients who suffer said condition are treated with different therapeutic alternatives. Amongst other functions, the kidneys are responsible, together with the liver, for activating vitamin D (vitD), which plays an important role in calcium homeostasis. Patients with renal impairment therefore present a vitD deficiency and, as a result, this is the first pharmacological treatment to be introduced.

Renal impairment, together with treatment of the disease, leads to hypercalcaemia and hyperphosphataemia. Consequently, patients with kidney failure are treated with phosphate binderphosphate binders to reduce the phosphate concentration in blood and calcimimetics to control the calcium levels in plasma by controlling parathormone (PTH) levels. The phosphate binderphosphate binders described include sevelamer and various salts of lanthanum, iron, calcium and other metals. The main calcimimetics are cinacalcet and KAI-4169.

Moreover, other types of co-medications that are administered in renal impairment to regulate blood pressure, cholesterol, diuretic use, sodium thiosulfate or bisphosphonates also exist.

Hypercalcaemia and hyperphosphataemia may cause cardiovascular calcification, although a deficiency of repressor factors (such as matrix Gia protein, osteopontin, fetuin, vitamin K) or an imbalance in promoting factors (vitamin D, FGF23, inflammatory cytokines, lipid deposits, apoptotic bodies, nucleational complexes, etc.) may delay or accelerate the process. Patients with renal impairment are commonly described as patients with CKD-MBD (chronic kidney disease mineral bone disease)as altered kidney function provokes a cascade of effects that also affect bone remodelling.

It has been shown that the degree of coronary artery calcification is related to lower survival and a higher number of cardiovascular events (R S Shantouf, Mi Budoff, N Ahmadi, A Ghaffari, F Flores, A Gopal, N Noori, Jing, C P Kovesdy, K Kalantar-Zadeh. Total and Individual Coronary Artery Calcium Scores as Independent Predictors of Mortality in Hemodialysis Patients. Am J Nephrol 2010; 31:419-425).

Specifically, it was shown that patients with no measurable coronary artery calcification (CAC=0) present a lower percentage of cardiovascular events and a lower mortality. As the CAC score increases, the number of cardiovascular events also increases and survival decreases.

Moreover, Russo et al. (D Russo, S Corrao, Y Battaglia, M Andreucci, A Caiazza, A Carlomagno, M Lamberti, N Pezone, A Pota, L Russo, M Sacco, B Scognamiglio. Progression of coronary artery calcification and cardiac events in patients with chronic renal disease not receiving dialysis. Kidney Int 2011; 80:112-118) demonstrated that a faster progression of vascular calcification is correlated with a lower survival and higher risk of cardiovascular accidents.

As such, cardiovascular events, including death, are related to both parameters:
Degree of vascular calcification.
Speed of progression of said vascular calcification.

There are currently no approved therapies which have demonstrated a higher survival or lower cardiovascular accident rate in dialysis patients, and the need to treat different diseases associated with renal impairment, resulting from the calcification process in the body and an imbalance in bone remodelling, remains, Various compounds the structure of which contains phosphorus (pyrophosphate, bisphosphonates, inositol phosphates, hexametaphosphate, etc.) have been reported to inhibit the formation of calcium-containing crystals. Some of the compounds in this large family containing C—O—P bonds have been found to inhibit various types of calcification, although it has not yet been demonstrated that these therapies are useful in the presence of renal impairment as known studies have either been with normal kidney function or, in the case of uraemia, said compounds have not been found to be effective.

DESCRIPTION OF THE INVENTION

Unexpectedly, the inventors of the present invention have found a form for prolonged administration in individuals with kidney failure that allows the efficacy of compounds of formula I, which would otherwise not be effective in individuals with uraemia, to be re-established. Said prolonged administration contrasts with a bolus- or short infusion-type administration and allows adequate levels of these compounds to be maintained or even re-established in blood for an adequate period of time. As a result, the kidney damage-related diseases are prevented, treated, inhibited and/or mitigated, or the progression thereof is prevented, in either the early stages of said diseases or when they are already established.

Thus, one embodiment of the present invention relates to use of at least one compound of formula I, or a pharmaceutically acceptable salt thereof:

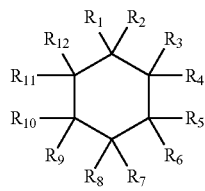

where:

each of $R_1$ to $R_{12}$ independently represents H, —X, —OX, —NHX, —NX$_2$, —SX, —OSO$_3$HX, —OSO$_3$X$_2$ or a compound of formula II:

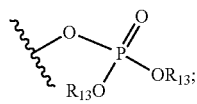

where each X independently represents H, $C_{1-30}$alkyl, $C_{2-30}$alkynyl or $Cy_1$, where $C_{1-30}$alkyl, $C_{2-30}$alkenyl and $C_{2-30}$alkynyl are independently optionally substituted with one or more $R_{14}$ and where $Cy_1$ is optionally substituted by one or more $R_{15}$;

$Cy_1$ represents a carbocyclic or heterocyclic three- to 10-membered ring, which may be saturated, partially unsaturated or aromatic, where said heterocycle has between one and four heteroatoms selected from amongst O, S and N, where said ring can be bound to the rest of the molecule via any available C atom and where $Cy_1$ is optionally fused to between one and four five- or six-membered rings, each saturated, partially unsaturated or aromatic, carbocyclic or heterocyclic, and where said fused heterocycle may contain one or two heteroatoms selected from amongst O, N and S; each $R_{13}$ independently represents H, $C_{1-30}$alkyl, —NH$_2$, —NHC$_{1-30}$alkyl or N(C$_{1-30}$alkyl)$_2$, where each $C_{1-30}$alkyl is independently optionally substituted with one or more halogen, —OH, —CN and —NO$_2$ groups; and each $R_{14}$ and $R_{15}$ independently represents —OH, $C_{1-30}$alkoxy, $C_{1-30}$alkyithionyl, $C_{1-30}$acyloxy, phosphate, halogen, trihaloC$_{1-30}$alkyl, nitrile azide, with the condition that at least one of $R_2$ to $R_{12}$ independently represents a compound of formula II, for the manufacture of a medicament for the treatment of a kidney failure-related disease in a subject with kidney failure characterised in that said medicament is administered in a prolonged release form.

In another embodiment the invention relates to the use defined above, where: Each X preferably independently represents H, $C_{1-30}$alkyl or $Cy_1$, where $C_{1-30}$alkyl is optionally substituted by one or more $R_{14}$ and where $Cy_1$ is optionally substituted by one or more $R_{15}$; and each $R_{14}$ and $R_{15}$ independently represents —OH, $C_{1-30}$alkoxy, $C_{1-30}$alkyithionyl, $C_{1-30}$acyloxy, phosphate, halogen, trihaloC$_{1-30}$alkyl, nitrile or azide.

In another embodiment the invention relates to the use defined above, where: each X represents H, $C_{1-30}$alkyl or $Cy_1$.

In another embodiment the invention relates to the use defined above, where: each X represents H.

In another embodiment the invention relates to the use defined above, where:

At least one of radicals $R_1$, $R_3$, $R_5$, $R_7$, $R_9$ and $R_{11}$ independently represents a compound of formula II:

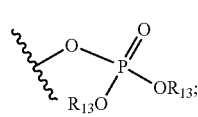

each $R_{13}$ independently represents H, $C_{1-30}$alkyl, —NH$_2$, —NHC$_{1-30}$alkyl or —N(C$_{1-30}$alkyl)$_2$, where each $C_{1-30}$alkyl is independently optionally substituted by one or more halogen, —OH, —CN and —NO$_2$ groups; and $R_2$, $R_4$, $R_6$, $R_8$, $R_{10}$ and $R_{11}$ independently represent H.

In another embodiment the invention relates to the use defined above, where:

$R_1$, $R_3$, $R_5$, $R_7$, $R_9$ and $R_{11}$ independently represent a compound of formula II:

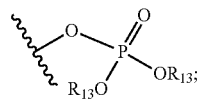

each $R_{13}$ independently represents H or $C_{1-30}$alkyl, where each $C_{1-30}$alkyl is independently optionally substituted by one or more halogen, —OH, —CN and —NO$_2$ groups; and $R_2$, $R_4$, $R_6$, $R_8$, $R_{10}$ and $R_{12}$ independently represent H.

In another embodiment the invention relates to the use defined above, where:

$R_1$, $R_3$, $R_5$, $R_7$, $R_9$ and $R_{11}$ independently represent a compound of formula

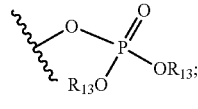

each $R_{13}$ independently represents H or $C_{1-30}$alkyl; and $R_2$, $R_4$, $R_6$, $R_8$, $R_{10}$ and $R_{12}$ independently represent H.

In another embodiment the invention relates to the use defined above, where:

$R_1$, $R_3$, $R_5$, $R_7$, $R_9$ and $R_{11}$ independently represent a compound of formula II:

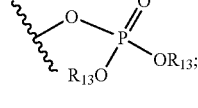

each $R_{3.3}$ independently represents H; and $R_2$, $R_4$, $R_6$, $R_8$, $R_{10}$ and $R_{12}$ independently represent H.

In a further embodiment the invention relates to the use defined above, where the compound of formula is inositol hexaphosphate (IP6).

Inositol phosphate can form other inositol phosphates (IP5, IP4, IP3, IP2, IP1 or inositol) by dephosphorylation in vivo. Inositol is assumed to mean any isomeric form of the molecule.

All compounds of formula I contain C—O—P bonds. Said bond provides said compounds with an affinity for calcium-containing crystals and a sufficiently labile bond to be hydrolysed in vivo, thereby preventing irreversible binding to calcium-containing crystals such as the hydroxyapatite (HAP) in bone, which would have a negative impact on bone remodelling, as is the case with bisphosphonates when administered long term as said compounds contain P—C—P bonds that cannot be hydrolysed by the body.

At the other extreme are phosphorylated compounds that do not contain said C—O—P bonds, such as pyrophosphates, the P—O—P bonds of which mean that they are too readily hydrolysed in the intestine, thus meaning that only parenteral administration is feasible.

The compounds of the present invention, with C—O—P bonds, represent an adequate midpoint due to the efficacy thereof and the fact that the body presents mechanisms for eliminating said compounds, thus reducing the risk of side effects.

In this sense, the inventors have demonstrated that said compounds bind rapidly to their receptor, thereby allowing the compound to achieve maximum binding in a relatively short period of time, and that said binding is reversible, thus meaning that the compound can be eliminated from the surface of the receptor over a reasonable period of time. This fact represents an enormous difference with regard to compounds with P—C—P bonds, which in vivo may present half-lives of several months on the surface of their receptor, for example in bone, thereby affecting bone remodelling.

In another embodiment the invention relates to the use defined above, which also comprises a compound selected from amongst a calcimimetic compound: vitamin B, vitamin D and vitamin K; phosphorus (phosphate) chelators; thiosulfate, a diuretic, preferably thiazide or indapamide; bisphosphonate or a pharmaceutically acceptable salt thereof; pyrophosphate; citrate, an antihypertensive and anticholesteraemic agent, The diuretic compounds preferably include thiazide or indapamide.

In another embodiment the invention relates to the use defined above, which also comprises vitamin D and/or K.

Throughout the present invention, the term "$C_{1-30}$alkyl", as a group or part of a group, refers to a linear or branched chain alkyl group containing between 1 and 30 carbon atoms including, amongst others, methyl, ethyl, propyl, isopropyl, butyl, isobutyl, sec-butyl, tert-butyl, pentyl, hexyl, decyl and dodecyl groups.

The term "$C_{2-30}$alkenyl" refers to a linear or branched alkyl chain containing between 2 and 30 carbon atoms and also contains one or more double bonds. Examples include, amongst others, ethenyl, 1-propenyl, 2-propenyl, isopropenyl 1-butenyl, 2-butenyl, 3-butenyl and 1,3-butadienyl.

The term "$C_{2-30}$alkynyl" refers to a linear or branched alkyl chain containing between 2 and 30 carbon atoms and also contains one or more triple bonds. Examples include, amongst others, ethynyl, 1-propynyl, 2-propynyl, 1-butynyl, 2-butynyl, 3-butynyl and 1,3-butadiynyl.

A $Cy_1$ group relates to a three- to 10-membered carbocyclic or heterocyclic ring that may be saturated, partially unsaturated or aromatic and which is bound to the rest of the molecule via any available C atom. When heterocyclic, $Cy_1$ contains between one and four heteroatoms selected from amongst N, O and S. Moreover, $Cy_1$ may optionally be fused with up to four five- or six-membered carbocyclic or heterocyclic rings, which may be saturated, partially unsaturated or aromatic. If the fused ring is a heterocycle, said ring contains one or two heteroatoms selected from amongst N, O and S. Examples of $Cy_2$ include, amongst others, phenyl, naphthyl, thienyl, furyl, pyrrolyl, thiazolyl, isothiazolyl, imidazolyl, pyrazolyl, 1,2,3-triazolyl, 1,2,4-triazolyl, tetrazolyl, 1,3,4-thiadiazolyl, 1,2,4-thiadiazolyl, pyridyl, pyrazinyl, pyrimidinyl, pyridazinyl, benzimidazolyl, benzofuranyl, isobenzofuranyl, indolyl, isoindolyl, benzothiophenyl, benzothiazolyl, cyclopropyl, cyclobutyl, cyclopentyl, cyclohexyl, cycloheptyl, azetidinyl and aziridinyl.

A $C_{1-30}$alkoxy group as a group or part of a group refers to an —O$C_{1-30}$alkyl group, where the $C_{1-30}$alkyl part has the same meaning as above. Examples include methoxy, ethoxy, propoxy, isopropoxy, butoxy, isobutoxy, sec-butoxy and tert-butoxy.

A $C_{1-30}$alkylthionyl group as a group or part of a group refers to an —SO$C_{1-30}$alkyl group, where the $C_{1-30}$alkyl part has the same meaning as above. Examples include methylthionyl, ethylthionyl, propylthionyl, isopropylthionyl, butylthionyl, isobutylthionyl, sec-butylthionyl and tert-butylthionyl.

A $C_{1-30}$acyloxy group as a group or part of a group refers to a —CO$C_{1-30}$alkyl group, where the $C_{1-30}$alkyl part has the same meaning as above. Examples include acetyl, ethanoyl, propanoyl and 2,2-diisopropylpentanoyl.

A halogen radical or the halo abbreviation thereof refers to fluorine, chlorine, bromine and iodine.

A trihalo$C_{1-30}$alkyl group signifies a group resulting from the substitution of three hydrogen atoms of a $C_{1-30}$alkyl group by three halogen radicals as defined above. Examples include, amongst others, trifluoromethyl, tribromomethyl, trichloromethyl, triiodomethyl, trifluoroethyl, tribromoethyl, trichloroethyl, triiodoethyl, tribromopropyl, trichloropropyl and triiodopropyl.

An —NH$C_{1-30}$alkyl group signifies a group resulting from the substitution of one hydrogen atom of an —NH$_2$ group by a $C_{1-30}$alkyl group as defined above. Examples include, amongst others, methylamine, ethylamine, propylamine, butylamine and pentylamine.

—N($C_{1-30}$alkyl)$_2$ signifies a group resulting from the substitution of two hydrogen atoms of an —NH$_2$ group by a $C_{1-30}$alkyl group as defined above. Examples include, amongst others, dimethylamine, diethylamine, diisopropylamine, dibutylamine and diisobutylamine.

The expression "optionally substituted by one or more" signifies the possibility that a group may be substituted by one or more, preferably by 1, 2, 3 or 4 substituents, more preferably by 1, 2 or 3 substituents and even more preferably by 1 or 2 substituents provided said group has sufficient positions that can be substituted available. If present, said substituents may be the same or different and may be located at any available position.

A further aspect of the present invention relates to use of a composition comprising at least one compound of general formula I as described above and another active substance and/or a pharmaceutically acceptable vehicle.

The active substance is selected from the list comprising a calcimimetic, vitamin, phosphate binder, thiosulfate, bisphosphonate, pyrophosphate, citrate, a diuretic, antihypertensive and anticholesteraemic agent to manufacture a medicament for the treatment and/or prevention of a kidney failure-related disease in a subject with kidney failure characterised in that said medicament)s administered in a prolonged release form.

Said compounds are normally used to treat kidney damage-related diseases. CKD-MBD always has a calcium and phosphorus metabolism imbalance, which results in hypercalcaemia and hyperphosphataemia, as an underlying problem and there comes a stage when bone, which mainly consists of HAP (calcium phosphate), can no longer act as a buffer for said excess calcium and phosphorus in the blood, thus meaning that calcium-containing crystals are deposited in different tissues and organs in the body. As a result, the different drugs in the previous paragraph act at different levels but with a single objective, namely to help control said calcium and phosphorus metabolism imbalance.

Several of the compounds described as active substances change the thermodynamics of the crystailisation process by modifying the concentration of the ions present in the structure of the calcium-containing crystal that is directly or indirectly responsible for the kidney failure-related disease. This sub-group includes calcimimetics, phosphate binder, thiosulfate, vitD and diuretics.

Calcimimetics allow the calcium and phosphate concentration to be controlled by regulating blood PTH levels. Said compounds include cinacalcet, NPS R-467, NPS R-568, KAI-4169.

Thiosulfate is a chelator that reduces the free calcium concentration in blood.

Although with a different mechanism of action, vitD has a similar effect. The vitD is preferably selected from the list comprising calciferol, ergocalciferol (Vit D2), cholecalciferol (Vit D3), doxercalciferol, paricalcitol alfarol or alpha-calcidol calcidiol, calcitriol, or derivatives or pharmaceutically acceptable salts thereof.

Phosphate binders act gastrointestinally by sequestering phosphate before it can be absorbed, thereby reducing the systemic concentration thereof in blood. The phosphate binder may contain a metal or be metal-free. The metal-free chelators include sevelarner, Metal-containing chelators include various calcium, iron, lanthanum, aluminium and magnesium salts.

Diuretics also affect the thermodynamics as altering the volume changes the calcium and phosphate concentration. The diuretic will preferably be a thiazide, thiazide-like (indapamide, chlortalidone, metolazone, etc.), a loop diuretic (bumetanide, etacrynic acid, furosemide, torsemide, etc.), carbonic anhydrase inhibitor, osmotic diuretic, potassium-sparing diuretic, etc. The thiazide will preferably be chlorothiazide, epithiazide, bendrofiumethiazide or hydrochlorothiazide.

The remaining compounds (pyrophosphate, citrate, bisphosphonates, antihypertensives, anticholesteraemic agents, vit B, vit K) act against the altered calcium and phosphate metabolism kinetically by attempting to stop the crystallisation process or altering bone metabolism by increasing the amount of repressor factors (pyrophosphate, citrate, vit B, vit K, bisphosphonates) or by reducing the quantity of promoter factors (necrotic remains or organic matter in the case of antihypertensives or lipid deposits in the case of anticholesteraernic agents).

The bisphosphonate may contain nitrogen or be nitrogen-free. Said bisphosphonate will preferably be selected from the list comprising etidronate, alendronate, risedronate, zoledronate, tiludronate, pamidronate, monidronate, neridronate, pamidronate, olpadronate, clodronate, ibandronate.

The antihypertensive will preferably be a diuretic (listed above), an adrenergic blocker (beta blocker, alpha blocker, mixed a calcium channel blocker (dihydropyridine or nondihydropyridine), a renin inhibitor, an angiotensin-converting enzyme inhibitor, an angiotensin II receptor antagonist, an aldosterone antagonist, a vasodilator, an alpha-2 agonist or a blood pressure vaccine.

The anticholesteraemic agent will preferably be a statin, a fibrate, niacin, a be acid sequestrant, ezetimibe, lomitapide, phytosterols or orlistat.

In another embodiment the invention relates to a combined composition comprising at least one compound of formula as defined above and one or more useful drugs for use thereof alone, simultaneously or sequentially for the treatment of patients with kidney failure, preferably where the useful drugs are selected from amongst a calcimimetic, vitamin B, vitamin D and vitamin K, phosphate binder, diuretics or other such as a bisphosphonate or a pharmaceutically acceptable salt thereof, pyrophosphate, citrate, antihypertensive or anticholesteraemic agent.

In this report, the term "combined preparation" or "juxtaposition" signifies that the components of the combined preparation do not need to be present together, for example in a composition, such that said components may be available for application separately or sequentially. Consequently, the expression "juxtaposed" implies that said preparation is not necessarily a true combination in light of the physical separation of the components thereof.

The pharmaceutical composition of the invention may also comprise one or more excipients.

The term "excipient" refers to a substance which helps absorption of the elements of the pharmaceutical composition of the invention, stabilises said elements, activates or helps preparation of the composition in the sense of conferring consistency or providing flavours that make said composition more palatable. Thus, the excipients may have a role maintaining the ingredients combined, such as starches, sugars or celluloses for example, as a sweetener, as a colourant, protecting the composition, such as isolating it against air and/or moisture, as a filler for a tablet, capsule or any other presentation, as a disintegrant to ensure dissolution of the components and absorption thereof in the intestine, without excluding any other type of excipient not mentioned in this paragraph.

As is the case for the excipient, the "pharmaceutically acceptable vehicle" is a substance used in the composition to dilute any of the components contained therein to a determined volume or weight. The pharmaceutically acceptable vehicle is an inert substance or a substance with an analogous action to any of the elements comprising the pharmaceutical composition of the present invention. The role of said vehicle is to allow the incorporation of other elements, allow better dosing and administration or to provide consistency and shape to the composition.

A further aspect of the present invention relates to a method for treating patients with kidney failure comprising the administration of a prolonged release (non-bolus) form of a therapeutically effective amount of a compound of formula I or a pharmaceutically acceptable salt thereof.

In the present invention, the term "kidney failure-related disease" refers to disease processes of a widely diverse nature in individuals with kidney damage and may refer, but is not limited, to any disease related to calcium or calcium metabolism disorders, such as renal lithiasis, cardiovascular calcification, cardiovascular disease, osteoporosis, bone cancer, podagra, calcific tendinitis, calcinosis cutis, rheumatoid arthritis, bone mineral disease, osteomalacia, adynamic bone, calciphylaxis.

Other kidney failure-related diseases may be of the cardiovascular type, such as, but not limited to, coronary disease, heart failure, cardiac disease, atherosclerosis, arteriosclerosis, thrombosis, hypertension, myocardial infarction, aneurysm, angina pectoris, peripheral vascular disease and cerebrovascular disease. The patient with renal impairment may suffer a cardiovascular accident, event or disease (ischaemia, arrhythmia, myocardial infarction, stroke, etc.).

An important concept is that various disorders, including those listed in the previous paragraphs, may be treated by preventing, reducing, slowing or stopping the progression of calcification in the presence of uraemia. The disease related to calcium disorders, or the calcification induced by said disease, may already be present when administration commences, in order to reduce or stop progression of the disease, or may not yet be present, in order to prevent the appearance or onset of the disease.

In the present invention, the term "kidney failure" or "renal impairment" refers to a subject with diminished kidney function (GM) in any of stages 1 to 5 thereof, with acute kidney injury or acute-over-chronic renal failure.

In the present invention, the term individual or subject refers to any animal species, including humans.

In the present invention, the term "prolonged release", slow release, non-bolus, refers to an administration form that slowly releases the compound into the bloodstream, thus allowing significant levels to be maintained in plasma for a longer period of time than for a "bolus-type" administration. A bolus-type administration comprises fast intravenous injection, for example less than 10 seconds, or intravenous infusion over less than approximately 3 minutes.

In an embodiment of the present invention, the prolonged release allows therapeutically adequate levels to he maintained in blood for at least 30 minutes. In the case of inositol phosphates, said adequate levels will preferably be higher than 0.15 micromolar (µM), more preferably higher than 0.3 µA and even more preferably higher than 0.6 µM.

The inventors have unexpectedly discovered, and with comparative tests, that the efficacy of treatment for vascular calcification that can be achieved under conditions of normal kidney function disappears when the subjects present renal impairment (uraemia). Consequently, it is described for the first time that a non-bolus type administration to achieve adequate therapeutic levels and maintain said levels for an adequate period of time is particularly useful and also allows the side effects to be reduced, thereby improving the safety profile of the product. Said non-bolus administration can be given in a period of 24 hours, preferably in a period of 4 hours, more preferably in a period of 20 minutes and even more preferably in a period of 5 minutes. In any case, although administration occurs over a short period of time, the most important aspect is that release of the compound into the blood is prolonged in time, of the non-bolus type, and should allow therapeutic levels to be maintained in blood for at least 30 minutes, preferably for more than 1 hour, more preferably for more than 3 hours and even more preferably for more than 4 hours.

An important aspect of the present invention consists of the treatment of subjects with renal impairment to prevent or treat a calcium disorder-related disease. Although compounds with C—O—P bonds have been described to inhibit the crystallisation of calcium-containing salts, the use thereof in subjects with renal impairment and as a non-bolus type administration is novel. For example, inositol hexaphosphate (IP6) has been described for the treatment of kidney stones in rats with normal kidney function (F Grases, B Iserm, P Sanchis, J J Torres, A Costa-Bauzà, A. Phytate acts as an inhibitor of renal calculi. Front Biosci 2001; 12:2580-2587), but the effect thereof on kidney stone formation in subjects with renal impairment has never been demonstrated, with said use being completely novel. Various recent attempts to demonstrate the efficacy of such compounds in calcium disorder-related diseases in the presence of uraemia have failed, leading to the conclusion by persons skilled in the art that such compounds are not useful for treating said diseases in the presence of renal impairment.

The inventors have unexpectedly discovered that when compounds with formula I, containing C—O—P bonds, are administered to animals with uraemia, much lower levels in blood are achieved and for a shorter period of time. This finding contrasts completely with the understanding of a person skilled in the art. When a compound is administered under conditions of renal impairment, renal elimination of said compound is reduced when compared with the case of normal kidney function, with more severe renal dysfunction leading to slower elimination of said compound. Consequently, a person skilled in the art would expect that when a compound is administered to a subject with renal impairment, higher levels of said compound in blood would be obtained for a longer period of time in comparison with a subject with normal kidney function.

Unexpectedly, the inventors discovered that the behaviour of the compounds of formula I is exactly the opposite. The recent development of adequate analytical tools has allowed this surprising behaviour to be discovered (Perello J, Maraschiello C, Lentheric I, Mendoza P, Tur F, Tur E, Encabo M, Martin E, Benito M, Isern B. Method for the direct detection and/or quantification of at least one compound with a molecular weight of at least 200. PCT/EP2012/069878) as previous methods did not allow such compounds to be correctly quantified in biological matrices such as blood.

When a compound of formula I is administered to a subject, lower levels of said compound in blood or plasma are obtained, and in some cases said levels are undetectable. Administration of the same dose via the same route of administration to a subject with normal kidney function leads to higher levels in blood for a longer period of time.

The inventors discovered that elimination of said compounds in the presence of uraemia is much faster due to the greater metabolism of the compound. This finding explains why various attempts to demonstrate the efficacy of such compounds in the presence of uraemia failed as the compound was rapidly destroyed (metabolised), more so than under conditions of normal kidney function, and could not exert its therapeutic effect on the specific receptor and disease, in other words, the higher metabolic rate prevented therapeutic levels from being reached and maintained for a sufficient time to demonstrate efficacy.

The compounds or compositions of the present invention may be administered by any appropriate method that provokes a non-bolus type release or effect, such as intravascular (for example intravenous) infusion, other parenteral (subcutaneous, subcutaneous depot, intraperitoneal, intramuscular, intradermal, intrathecal, epidural, spinal or others known to a person skilled in the art), topical (intranasal, inhalation, intravaginal, transdermal or others known to a person skilled in the art), enteral (oral, sublingual, rectal, etc.) administrations, oral, spinal, intraperitoneal preparations or others known to a person skilled in the art.

In the particular case of oral administration, delivery technologies may be used to achieve higher levels in blood or to maintain said levels for a longer period of time in order to achieve or enhance the prolonged release (non-bolus) effect. As examples, said delivery techniques may include the use of liposomes, organic polymers, the formation of associations or ion pairs (for example quaternary ammonium salts). Additionally, delivery technologies may delay or modulate absorption of the compound and/or protect said compound from being metabolised in the gastrointestinal tract or during first hepatic pass prior to reaching the bloodstream and/or corresponding receptor, which may help to maintain exposure over time.

In the particular case of patients treated with dialysis, a very appropriate method of administration consists of a non-bolus type administration of the compound via the dialysis apparatus (before or after the filter) instead of directly injecting the compound into the patient intravenously. Thus, blood can be treated with the compound as it leaves the patient and circulates through the dialysis circuit and, when the blood containing the compound returns to the body, the compound has been introduced into the blood in a manner that presents a series of advantages.

This method of administration was unexpectedly discovered as a plausible alternative. A person skilled in the art would undoubtedly have thought that administration via the dialysis apparatus would not be possible as these compounds with a relatively low molecular weight should readily be lost via the dialysis membrane. Consequently, administering the compound via the dialysis system when the blood is outside the body would not be an alternative as the compound would be lost (dialysed) when passing through the filter (dialysis membrane) prior to reaching the body of the subject again. In the case of IP6, for example, the inventors unexpectedly found that said compound is not lost as it was discovered that binding of IP6 to proteins was in the range 70-90%, thus meaning that only 10-30% of the compound is available to be dialysed. However, and in addition, the high negative charge of the compound creates an electrostatic repulsion that prevents the passage thereof through the filter in a significant manner.

Moreover, the inventors showed that said compounds, preferably inositol phosphates, can chelate (sequester) free or ionic calcium in the bloodstream, thereby reducing the concentration thereof, which is necessary for said calcium to perform its biological role. Thus, calcium chelation is a problem when certain blood concentrations are reached. A non-bolus type administration is much more appropriate as said administration avoids concentration peaks and the effect on calcium chelation is eliminated.

Moreover, in the case of dialysis patients, administration via the dialysis apparatus allows the blood to equilibrate with the dialysis fluid prior to returning to the body; thus, although the compound containing C—O—P bonds may sequester ionic calcium, this fact is compensated when the blood passes through the dialysis filter thereby eliminating said side effect and significantly improving the safety profile.

As used in the present invention, the term "treatment" refers to countering the effects caused as a result of the disease or pathological condition of interest in a subject (preferably a mammal, and more preferably a human), including:
(i) inhibiting the disease or pathological condition, in other words slowing or stopping the development or progression thereof;
(ii) relieving the disease or pathological condition, in other words causing said disease or pathological condition, or the symptoms thereof, to regress;
(iii) stabilising the disease or pathological condition.

In an embodiment of the present invention, a synergistic effect is unexpectedly observed between a compound of formula I and other treatments for renal impairment selected from the list, as it has been observed that when a compound of formula I is combined with another that modifies the thermodynamics of the calcium-containing crystal formation or growth process a synergistic effect occurs. Moreover, it has been observed that combining a compound of formula I with another compound that modifies the kinetics of said process (reducing the promoter factors or increasing the repressor factors) also produces said synergy.

In general, the effective quantity of a compound of the invention administered will depend on the relative efficacy of the compound concerned, the severity of the disorder treated and the weight of the subject. Administration can range from daily to weekly, monthly, two monthly or any other frequency known to a person skilled in the art.

The word "comprises", and variants thereof, as used throughout the description and claims, is not intended to exclude other technical features, additives, components or steps. For a person skilled in the art, other subject matters, advantages and features of the invention will partially follow from the description and partially from the practice of the invention. The following examples and drawings are provided by way of illustration and are not intended to limit the present invention.

EXAMPLES

The invention will be illustrated below by way of several tests performed by the inventors which highlight the specificity and efficacy of the treatment method described.

Example 1

Compatible Combination of IP6 with Other Treatments for Renal Impairment

Objective: to evaluate the compatibility of IP6 with other treatments for renal impairment Experimental: Wistar rats were treated with IP6 (subcutaneous, s.c.), IP6 (s.c.)+sevelamer (oral), IP6 (s.c.)+cinacalcet (oral), IP6 (s.c.)+Vit D (s.c.), IP6 (s.c.)+sodium thiosulfate (s.c.), IP6 (s.c.)+ibandronate (s.c.).

Results and Discussion: no significant difference is observed between administration of IP6 alone or concomitantly with another treatment. It is concluded that concomitant administration of IP6 with other treatments for renal impairment does not imply compatibility problems.

Example 2

In vitro Determination of the Affinity of IP6 for Hydroxyapatite (HAP)

Objective: the objective of this study is to analyse the affinity of IP6 for the target thereof, thereby obtaining a curve for the affinity of IP6 for HAP.

Experimental: 4 different quantities of HAP were incubated with increasing concentrations of IP6 at 37° C., pH 7.4, for 4 hours while stirring continuously. The total quantity of IP6 bound to the surface of the target (HAP) was quantified.

Figure 1:
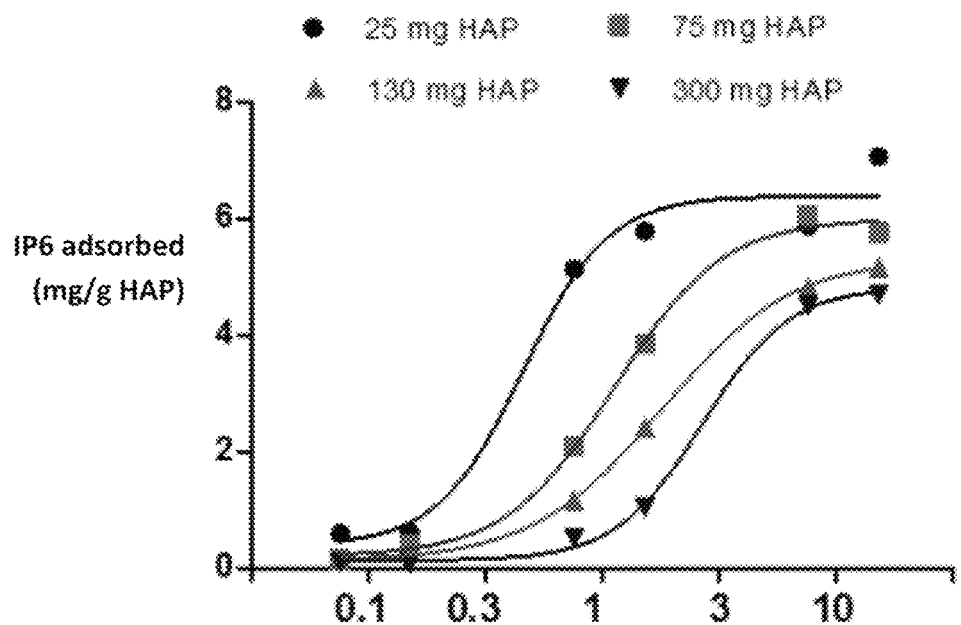
FIG. 1. Adsorption of IP6 to different concentrations of HAP crystals after incubation at 37° C., pH 7.4, for 8 h.

Results: a dose-dependent adsorption curve, with saturation at a concentration of 7.6 µM or higher, was obtained. The maximum adsorption of IP6 on the HAP surface ranges from 4.8 mg adsorbed when using 300 mg of the target to 6.42 mg when using 25 mg of HAP, and this maximum adsorption is achieved in the presence of 7.6 µM IP6 for 8 hours. To characterise the behaviour of IP6 binding, the $EC_{50}$ and $E_{max}$ for the adsorption thereof on HAP were calculated. This was performed using a non-linear regression model (Log[agonist] vs. response—slope variable; GraphPad Prism software). The $EC_{50}$ values calculated were 0.46 µM (25 mg HAP), 0.96 µM (75 mg HAP), 1.22 µM (130 mg HAP) and 2.09 µM (300 mg HAP). $E_{max}$ reached saturation at a value of 6.42 mg/g. The results are shown in FIG. 1.

Conclusions: IP6 has a high affinity for HAP and adsorption thereof on HAP crystals increases linearly up to 7.6 µM IP6, at which point the adsorption sites on the HAP surface are saturated.

Example 3

In vitro Determination of the Binding Kinetics of IP6 to HAP

Objective: to analyse the binding rate of IP6 to HAP.

Experimental: 130 mg HAP was incubated (in triplicate) with 7.6 µM IP6, at 37° C., pH 7.4, for different time intervals while stirring continuously.

Figure 2:
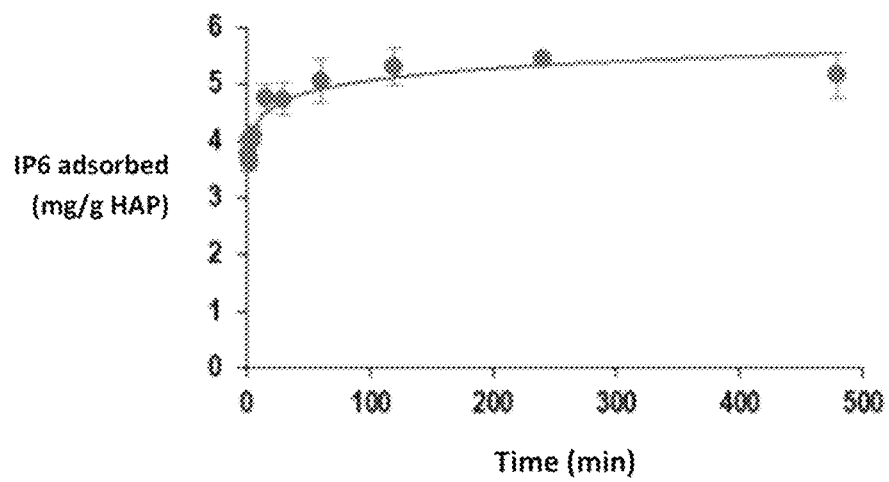
FIG. 2. Adsorption of IP6 to HAP crystals. IP6 (7.6 µM) was incubated in the presence of 130 mg HAP at 37° C., pH 7.4, for between 5 minutes and 8 hours.

Results and discussion: rapid binding of IP6 to HAP was observed (FIG. 2), with an adsorption maximum being reached at 60 minutes. Around 80% of maximum binding was achieved after 5 minutes.

Example 4

In vitro Affinity of IP6 for HAP Release Studies

Objective: to analyse the release rate of IP6 from HAP.

Experimental: 130 mg HAP was incubated in triplicate with 7.6 µM IP6, at 37° C., pH 7.4, for different time intervals while stirring continuously. Subsequently, the HAP with adsorbed IP6 was placed in an IP6-free solution and the amount of IP6 released from the surface thereof evaluated at different timepoints.

Figure 3:
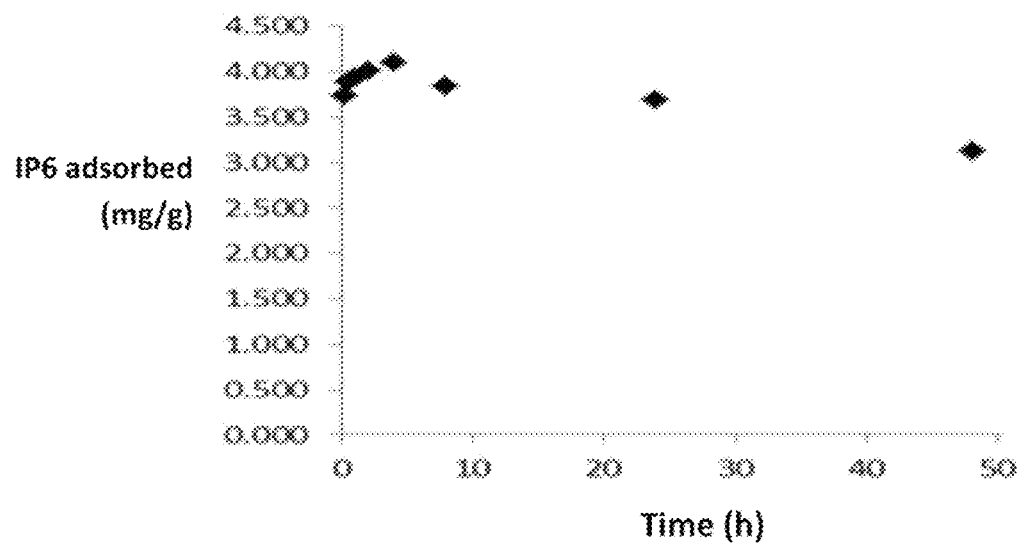
FIG. 3. Release kinetics of IP6 from the HAP surface. IP6 (7.6 µM) was incubated in the presence of 130 mg HAP and IP6 released at different timepoints up to 48 hours.

Results and discussion: a relatively slow release of IP6 from the HAP surface was observed (FIG. 3). After incubation for 2 days, 80% of the IP6 remained bound to the HAP surface.

Example 5

Pharmacokinetic (PK) Profile for IP6 Administered Subcutaneously (s.c.) to Rats with Normal Kidney Function and with Diminished Kidney Function Objective: to evaluate the PK profile for rats with normal kidney function and renal impairment.

Experimental: a single s.c. dose (10 mg/kg) was administered to rats with normal kidney function. Plasma samples were obtained at different timepoints up to 60 minutes. A different group of Wistar rats received oral treatment with adenine 600 mg/kg (p.o.) for 10 days to induce renal impairment. Alpha-calcidol (300 ng/kg) was administered on days 11 and 13 and plasma samples were collected at different timepoints up to 60 minutes on day 14. The plasma IP6 concentrations were quantified for both groups.

Figure 4:
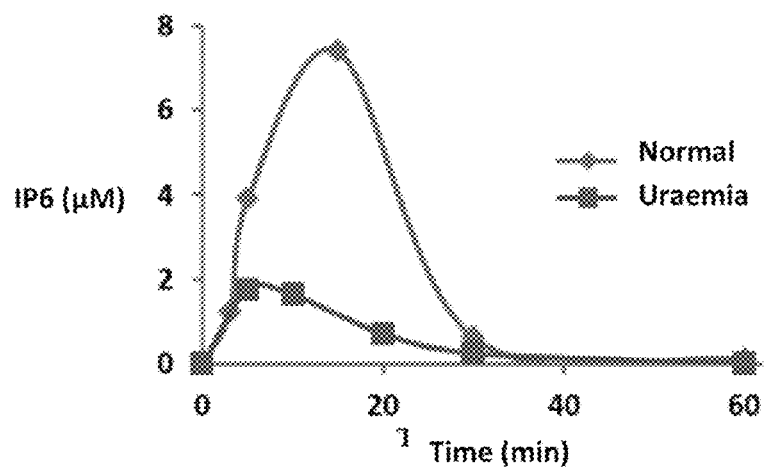
FIG. 4. PK profile for IP6 after s.c. administration of 10 mg/kg in normal and uraemic rats.

Results and discussion: the normal Wistar rats presented measurable levels for at least 30 minutes, with a peak concentration of 7.4 µM at 15 minutes post-administration. The uraemic rats showed a much lower exposure, with much lower levels at all timepoints and a peak concentration of 1.8 µM at 5 minutes post-administration (FIG. 4). Lower inositol phosphates (IP5, IP4, IP3, IP2, IP1) and inositol were detected as metabolites.

Conclusions: IP6 exposure in uraemic animals was lower than in normal animals, with a lower peak concentration for a shorter period of time. This effect is due to a higher metabolic rate in the presence of uraemia.

Example 6

Pharmacokinetic (PK) Profile for IP6 Administered to Rats with Normal Kidney Function and with Renal Impairment (Uraemia) by Prolonged Infusion Objective: to evaluate the PK profile for IP6 in rats with normal kidney function and non-dialysed rats with renal impairment by intravenous infusion.

Experimental: Wistar rats with normal kidney function were treated daily with a dose of 10 or 50 mg/kg IP6 by intravenous infusion over 4 h. Plasma samples were obtained at different timepoints up to 4 hours on day 0. The animals were then treated orally with 600 mg/kg (p.o.) adenine for 10 days to induce renal impairment. The animals were treated with alpha-calcidol (300 ng/kg) on days 11 and 13 and plasma samples were collected at different timepoints up to 4 hours on day 14. The plasma IP6 levels were quantified for both groups.

Figure 5:
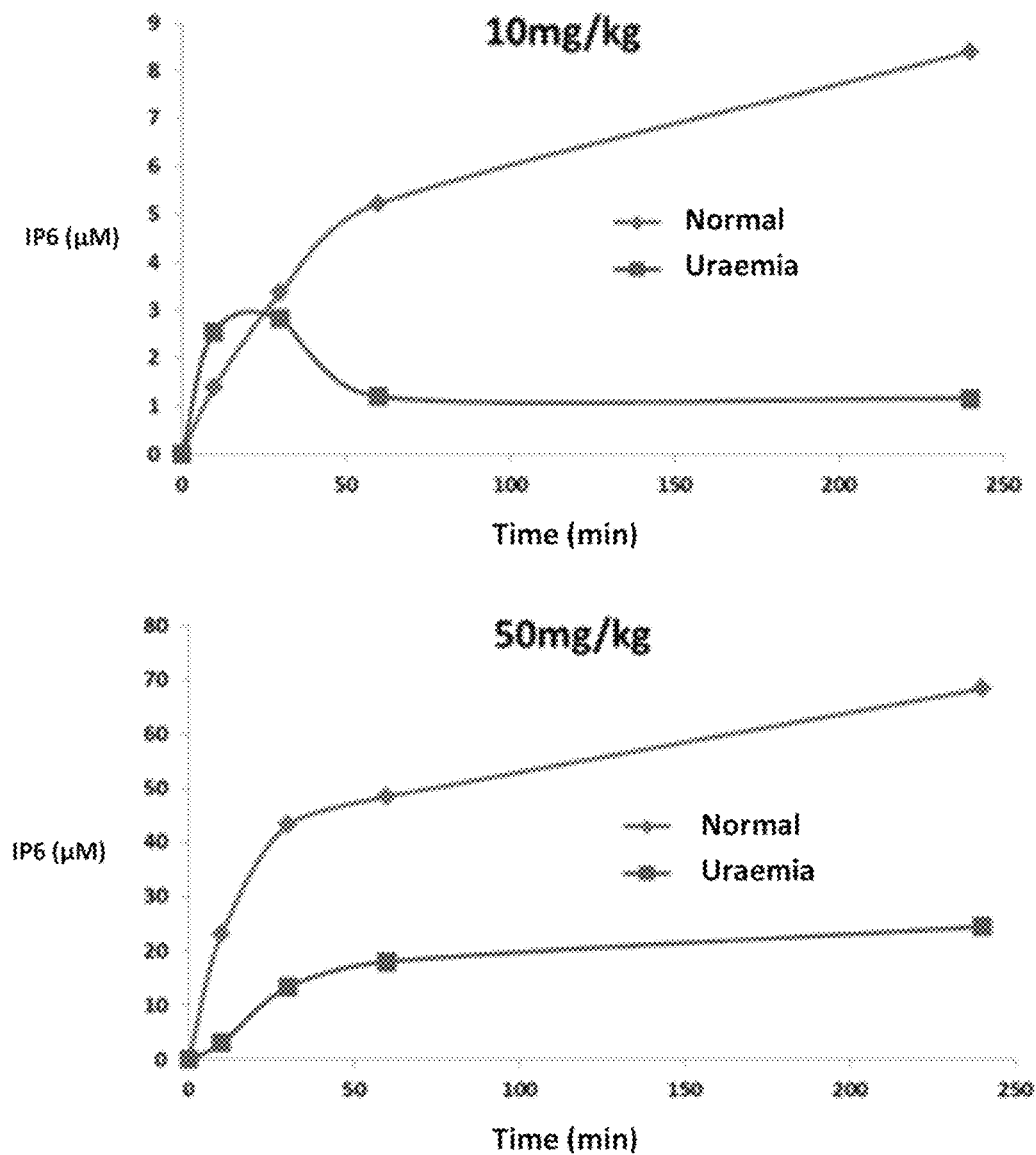
FIG. 5. PK profile for IP6 after intravenous infusion of 10 and 50 mg/kg in normal and uraemic rats for 4 h.

Results: the normal rats showed a peak plasma concentration of 8.4 and 68.4 µM at a dose of 10 and 50 mg/kg respectively. However, when rats were made uraemic, the peak concentration achieved at 10 mg/kg was 2.8 µM at 30 minutes, although said value decreased to 1.2 µM after 4 hours due to the high metabolic rate. The metabolic effect could be partially overcome at 50 mg/kg, with a peak plasma concentration of 24.6 μM being achieved at 4 hours and no decrease in plasma concentration after 30 minutes being observed, thus allowing an approximately constant concentration to be maintained for 3 hours (from hour 1 to hour 4) (FIG. 5). Although the final plasma concentration was lower than in normal rats, exposure remains significant and potentially sufficient to be effective, as explained in subsequent examples.

Conclusions: IP6 exposure in uraemic animals was lower than in normal animals, with a lower concentration being reached after 4 hours. However, if the dose is sufficiently high, prolonged infusion allows significant levels to be achieved for a prolonged period of time, partially overcoming the effect due to the high metabolic rate.

Example 7

Efficacy of IP6 Calcium-Related Diseases in Animals with Normal Kidney Function 7a. inhibition of vit D-induced (75,000 IU/kg×5) cardiovascular calcification by intravenous administration of IP6.

Objective: to evaluate the efficacy of intravenous IP6 in inhibiting vitamin D-induced cardiovascular calcification in rats.

Experimental: male Sprague Dawley (SD) rats were divided into 7 groups and IP6 was administered intravenously daily for 14 days at a dose of 0, 0,05, 0.1, 0.5, 1, 5 and 10 mg/kg. Calcification was induced by oral administration of 75,000 IU/kg vitamin D on treatment days 3 to 7. Samples were collected. On day 14 the aortas and hearts of the animals were collected to quantify calcification.

Figure 6A:
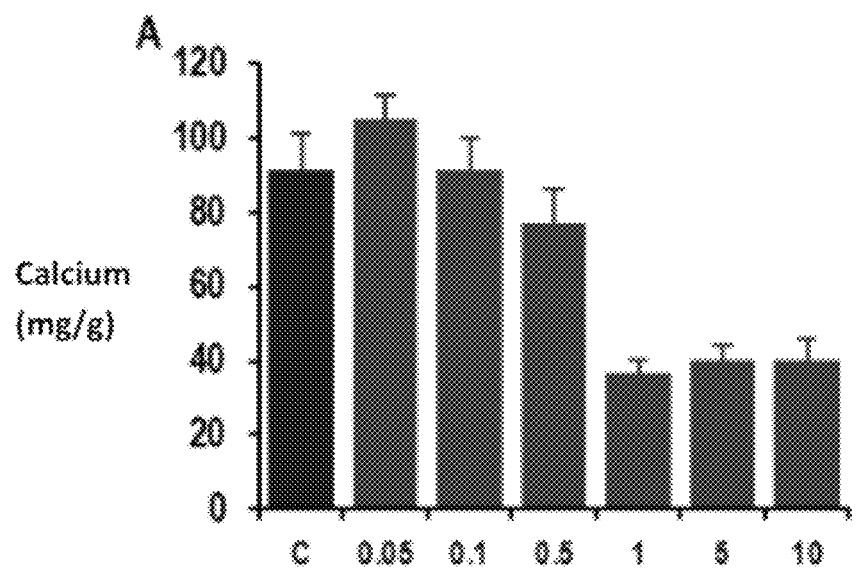
FIG. 6. Calcium content in aorta (A) and heart (B) after intravenous administration of IP6 in a vitamin D-induced cardiovascular calcification model in rat (5×75,000 IU/kg). Dose expressed in mgk; C=control group.
Figure 6B:
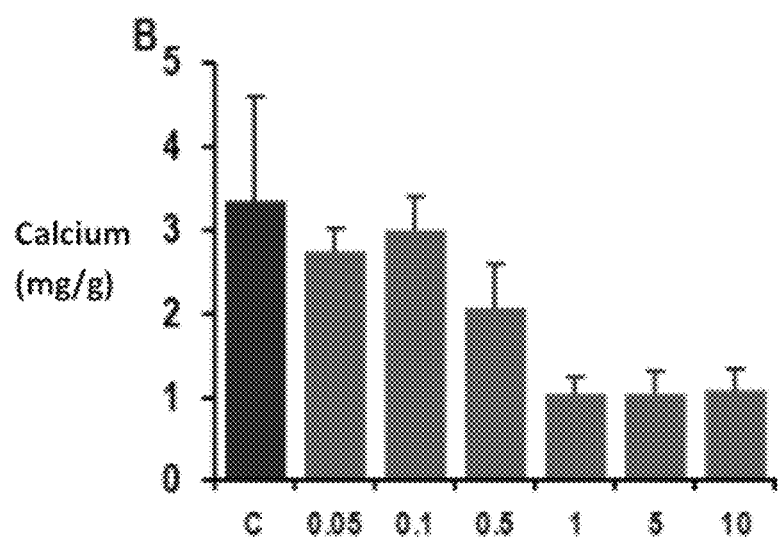

Results and discussion: administration of vitamin D induced a marked increase in calcification of the aorta and heart. Intravenous administration of 0.05 to 0.5 mg/kg IP6 did not affect the mineral content of the aorta and heart. However, administration of a dose of between 1 and 10 mg/kg reduced the calcification in both tissues by up to 60% in aorta and 68% in heart (FIG. 6).

7.b. Inhibition of vit D-induced (300,000IU/kg×3) cardiovascular calcification by s.c. IP6.

Objective: to evaluate the efficacy of s.c. IP6 for inhibiting vit D-induced cardiovascular calcification in rats.

Experimental: male SD rats were divided in 9 groups. Two of said groups (sham and control groups) received s.c. saline 2 ml/kg; 6 groups received s.c. IP6 at a dose of 0.1, 1, 10, 60 and 100 mg/kg (2 ml/kg) and another 35 ml/kg s.c. sodium pyrophosphate, PPi (2 ml/kg). One group was treated with a s.c. Alzet pump loaded with 200 mg/ml IP6. Calcification was induced by oral administration of 300,000 IU/kg vitamin D (2 ml/kg) for 3 days starting on treatment day 3. The sham group was treated with saline in a similar manner. The calcium content in heart, aorta and kidneys was determined after treatment for 7 days.

Figure 7:
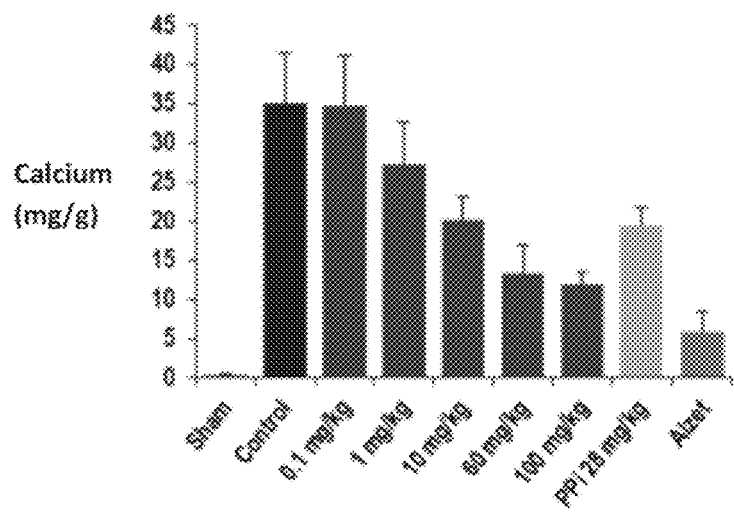
FIG. 7. Calcium content in aorta after s.c. administration of IP6 in a vitamin D-induced cardiovascular calcification model in rat (3×300,000 IU/kg).

Results and discussion: s.c. IP6 inhibited calcification, with a dose-response behaviour being obtained. The minimum dose that produced a significant effect was 10 mg/kg, which caused the same effect as 28 mg/kg pyrophosphate, with IP6 exhibiting a greater potency. Doses of 60 and 100 mg/kg exhibited an efficacy of approximately 60%. Treatment by prolonged administration using an Alzet pump resulted in an 85% reduction in calcification (FIG. 7).

Conclusions: s.c. IP6 inhibits aortic calcification in a dose-response manner, with an $EC_{50}$ of 3.75 mgkg and an $E_{max}$ of 65.5%. PPi exhibits good efficacy but at higher doses than IP6. Prolonged administration using an Alzet pump led to a significant increase in efficacy.

7.c. Evaluation of IP6 (s.c.) on the progression of vitamin D-induced vascular calcification (100,000 IU/kg×3) in a rat model for 2 weeks.

Objective: to evaluate the pharmacological profile of IP6 as regards the progression of vascular calcification.

Experimental: 48 SD rats were treated x3 with vitamin D (s.c. 100,000 IU/kg) to induce tissue calcification. Calcification was allowed to progress for 5 days, and treatment with 0, 10 or 60 mg/kg IP6 s.c. was administered from day 5 until day 14. Calcification of the kidneys and heart was evaluated.

Figure 8A:
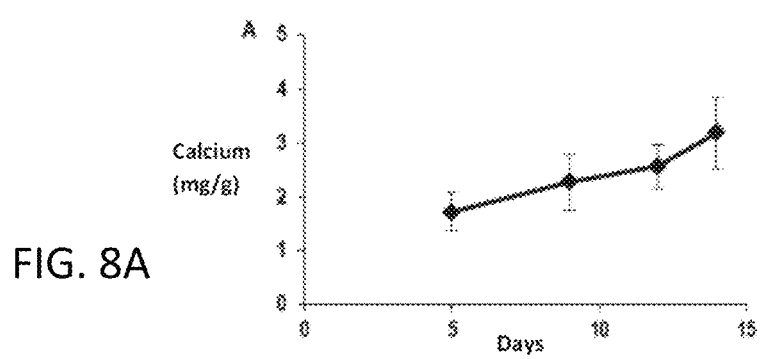
FIG. 8. (A) Progression of heart calcification and (B) inhibition of the progression of said calcification after s.c. treatment with 10 and 60 mg/kg IP6 on days 5 to 14. 100,000IU/kg vitamin D was administered on days 1, 2 and 3.
Figure 8B:
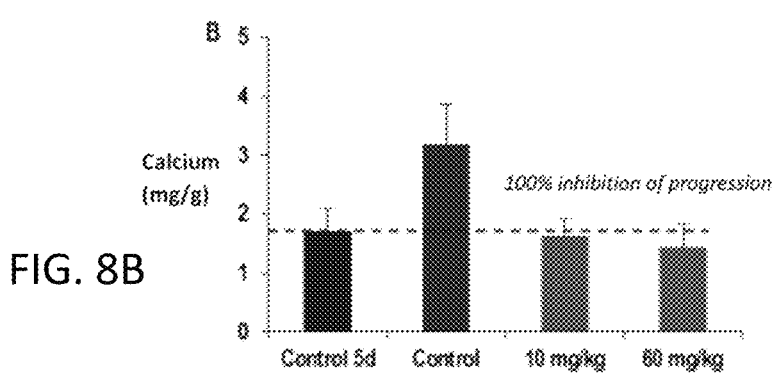
Figure 9A:
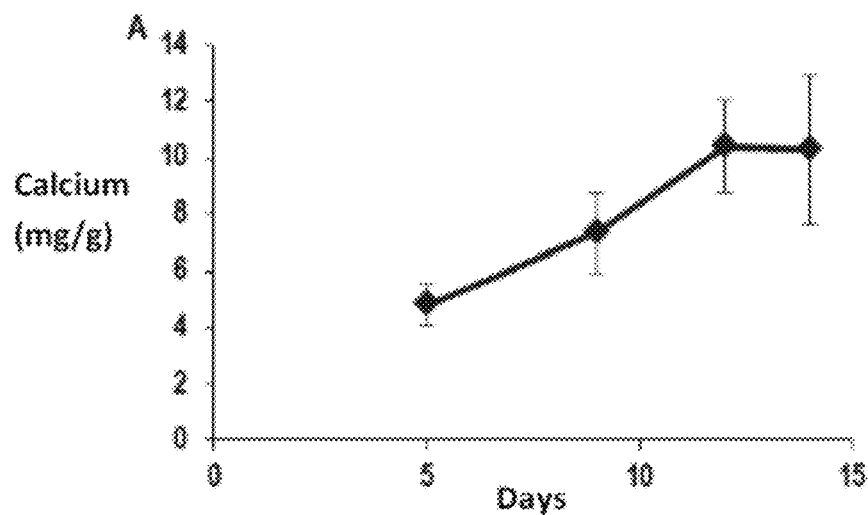
FIG. 9. (A) Progression of renal calcification and (B) inhibition of the progression of said calcification after s.c. treatment with 10 and 60 mg/kg IP6 on days 5 to 14. 100,000 IU/kg vitamin D was administered on days 1, 2 and 3.
Figure 9B:
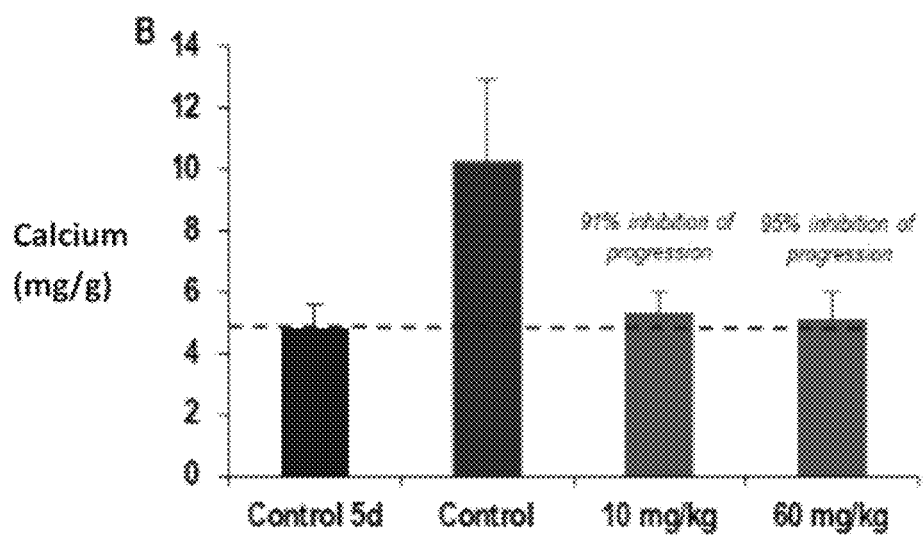

Results and discussion: tissue calcification clearly progressed from day 5 to day 14. Treatment with IP6 inhibited the progression of heart calcification by 100% (FIG. 8) and that of renal calcification by 95% (FIG. 9) at the highest dose. These findings demonstrate for the first time that IP6 can prevent calculus growth in vivo, even when said calculi are already formed and deposited in tissue.

Example 8

Efficacy of IP6 in calcium disorders in animals with renal impairment (uraemia)

8.a. Nephrectomy and administration of IP6 by i.v. bolus model

Objective: to determine the efficacy of intravenous IP6 in the prevention of tissue calcification in a chronic renal impairment model (5/6 nephrectomised rats).

Experimental: 48 SD rats were 5/6 nephrectomised by complete right lateral nephrectomy and 23 partial nephrectomy of the left kidney. 16 animals per group were treated intravenously (bolus) with 2 ml/kg saline, 1 mg/kg IP6 or 5 mg/kg IP6. The animals received a phosphate-rich diet (1% Ca, 1.2% P) containing 20% lactose. After 8 weeks the aorta, heart and remaining ⅓ kidney were collected and the tissue calcium content determined.

Results and conclusions: no evidence of calcification inhibition was observed when the animals were treated with IP6. Although the model presents high variability, as only a small percentage of control animals presented calcification and the surgical procedure is probably not very homogeneous, the high metabolic rate in the uraemic animals is the reason for the lack of efficacy.

8.b. Adenine and bolus-type s.c. administration model.

Objective: to determine the efficacy of IP6 in the prevention of tissue calcification in an animal model of chronic renal impairment (adenine).

Experimental: CKD was induced in 4 groups (n=12) of male Wistar rats by oral (p.o.) treatment with adenine (600 mg/kg/day) daily for 10 days. After treatment with adenine, the rats received alpha-calcidol at a dose of 300 ng/kg (3×/week, p.o.) until day 28. From day 0 until sacrifice (day 28), the animals were treated with a 2 ml/kg s.c. bolus of 0, 3, 10 and 30 mg/kg IP6. At each treatment, 3 additional animals were included to evaluate the PL for IP6. After 28 days the aorta, heart and right kidney were collected and the tissue calcium content determined.

Results and conclusions: no evidence of calcification inhibition was observed in any of the tissues. Although the model is reproducible and with consistent tissue calcification, the high metabolic rate of IP6 in uraemic animals is the reason for the lack of efficacy.

8.c. Adenine and non-bolus-type intravascular administration model.

Objective: to determine the efficacy of IP6 as a non-bolus type administration in the prevention of tissue calcification in uraemic animals.

Experimental: CKD was induced in 2 groups (n=12) of male Wistar rats by oral (p.o.) treatment with adenine (600 mg/kg/day) daily for 10 days. After treatment with adenine, the rats received alpha-calcidol at a dose of 300 ng/kg (3×week, p.o.) until day 28. From day 0 until sacrifice (day 28), the animals were treated with an intravascular infusion of 50 mg/kg IP6 or saline for 4 hours. After 28 days the aorta and heart were collected and the tissue calcium content determined.

Results and conclusions: treatment with IP6 led to an 80% and 85% reduction in average calcification in the aorta and heart respectively. Despite the high metabolic rate, which reduced the plasma IP6 levels by 90% by the end of the experiment, prolonged non-bolus type administration allowed the metabolic effect to be compensated and the efficacy of IP6 in a calcium disease under uraemic conditions to be proved for the first time.

Example 9

Calcium Chelation by IP6 In vitro

Objective: to evaluate the ionic calcium chelation potential of IP6.

Experimental: a 2.5 mM of calcium in NaCl 0.15 M, pH 7.40, was pipetted with increasing concentrations of IP6. The amount of free ionic calcium was measured potentiometrically using a calcium-selective electrode and a potentiometer.

Figure 10:
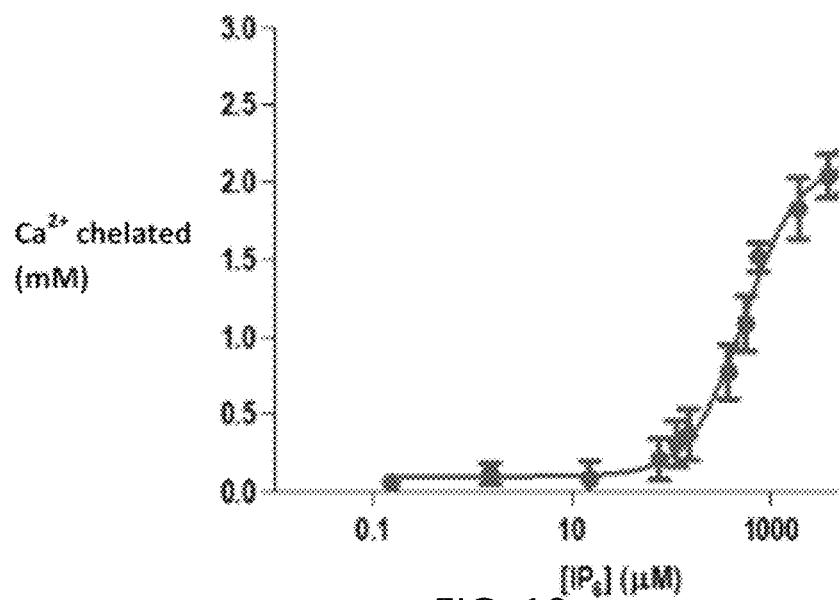
FIG. 10. Chelation of ionic calcium by IP& Increasing concentrations of IP6 were added to a 2.5 mM solution of calcium in 0.15 M NaCl, pH 7.4, and the ionic calcium levels measured.

Results and conclusions: IP6 exhibits a significant ionic calcium chelation ability above 379 µM. The semi-logarithmic representation of the dose-response curve (FIG. 10) shows a sigmoid profile, saturating at 3788 µM and with an $EC_{50}$ of 539 µM. These results are shown in FIG. 10. Said concentration is consistent with the levels observed in in vivo studies and explains why the side-effects of IP6 are related to hypocalcaemia (chelation of ionic calcium).

Example 10

Calcium Chelation by IP6 In vivo 10.1. The effects of IP6 on cardiovascular function after intravascular infusion in conscious dogs for 2 hours by telemetry.

Objective: to determine the effects of a non-bolus type administration of IP6 on the electrocardiogram (ECG) and serum ionic calcium concentrations.

Experimental: 4 male dogs were treated with 3, 10 and 30 mg/kg IP6 by infusion for 2 h in a Latin square design. A washout period of one week was performed between doses. ECGs were measured telemetrically at 1 h and 20 minutes prior to infusion and 5, 15, 30, 45 minutes, 1, 2, 6 and 24 h post-infusion. In a second stage, blood samples were taken for PK, for the same doses, at 20 minutes prior to infusion and 5, 15, 30 minutes and 1, 1,5, 2, 3 and 6 h post-infusion. In this case the washout period between doses was 2 days. Total and free calcium in the blood samples was also measured.

Results: the state of health, weight, cardiorespiratory function, ECG, body temperature and total and free potassium in blood were relatively unaffected by infusion of IP6 for 2 h for any dose. The mean blood ionic calcium concentrations were also unaffected. The peak IP6 levels found were 27, 150 and 482 µM for 3, 10 and 30 mg/kg respectively, Conclusions: infusion of IP6 at a dose of 3, 10 and 30 mg/kg for 2 h has no negative effects on dogs under the experimental conditions described.

10.2. The effects of IP6 on cardiovascular function after bolus-type intravenous administration in conscious dogs by telemetry.

Objective: to examine the effects of a bolus-type administration of IP6 in serum ionic calcium, ECG and clinical signs in dogs.

Experimental: 4 male dogs, 2 per dose, were injected with 10, 15 and 30 mg/kg. Two washout days were introduced between the different doses. The ECGs were recorded telemetrically.

Blood ionic calcium concentrations were determined on different days to the ECG measurements.

Figure 11:
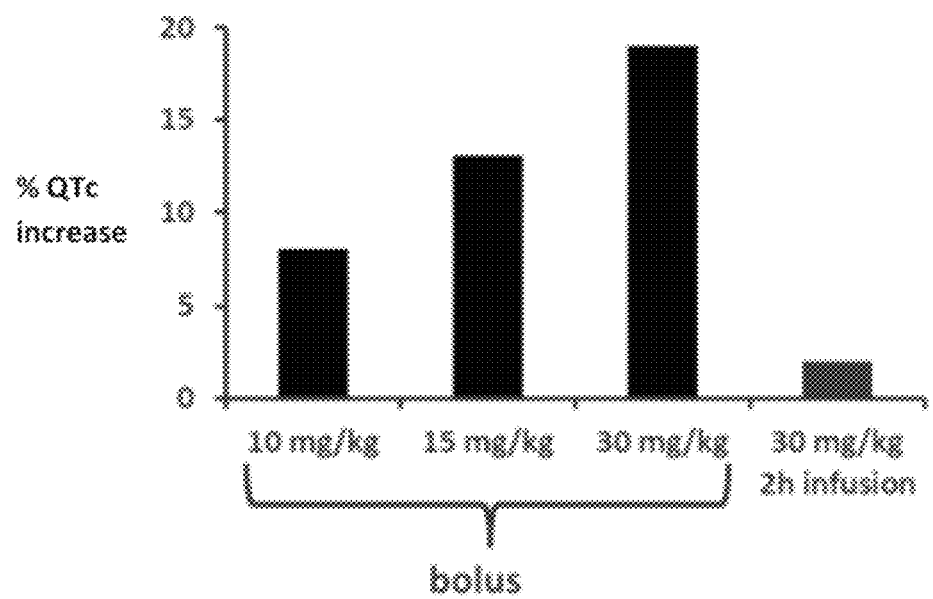
FIG. 11, Increase in the QTc interval after bolus and non-bolus type administration of IP6.

Results and conclusions: at a dose of 10 mg/kg IP6 has no significant effects on ECG parameters or ionic calcium concentrations. A mild tachycardia and prolonged QTc interval were observed above 15 mg/kg, becoming significant above 30 mg/kg (FIG. 11). This effect is correlated with a 30% decrease in ionic calcium. Hypocalcaemia is the cause of the prolonged QTc interval. These findings, together with those for infusion over 2 h in the previous example, confirm, that IP6 affects hypocalcaemia and prolongs the QTc interval depending on the peak plasma IP6 concentration as IP6 can chelate ionic calcium. Said effect can be corrected by increasing the administration period by way of a non-bolus type administration.

Example 11

Administration of IP6 Via the Dialysis System

Objective: to establish the dialysability of IP6 in human blood using a real dialysis system and the effect thereof on calcium chelation.

Experimental: 1 litre of human blood obtained from patients undergoing therapeutic phlebotomy was introduced into a recipient forming a closed dialysis circuit to simulate a real dialysis. Two experiments were performed (administration pre- and post-dialyser both in bypass and dialysis mode), administering IP6 to human blood for 20 minutes when outside the recipient (which simulated the animal or human body) and circulating via the dialysis circuit. The recipient containing 1 litre of whole blood at a controlled temperature of 37° C. is connected to the dialysis apparatus to form a closed circuit. The dialysis apparatus will be connected for 1 hour (dialysis fluid flow of 500 ml/min and blood flow of 350 ml/min). Blood samples are collected at different times to determine the IP6 and ionic calcium levels.

Figure 12:
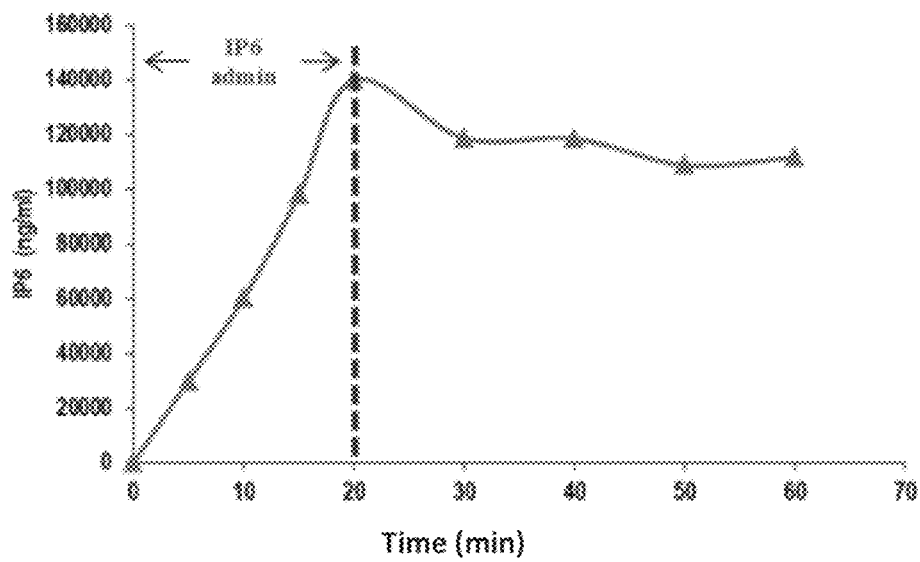
FIG. 12. IP6 concentrations in human blood after administration for 20 minutes via the dialysis circuit.

Results and conclusions: administration of IP6 via the dialysis line for 20 minutes using a standard dialysis apparatus, simulating the standard clinical procedure, shows that IP6 is not lost via the dialysis membrane (FIG. 12).

Figure 13:
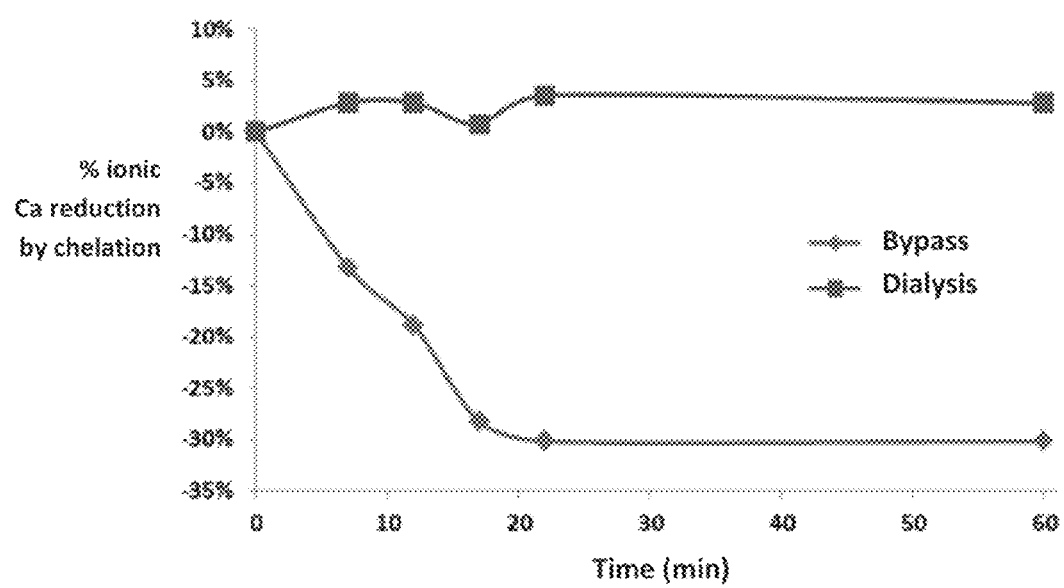
FIG. 13. Ionic calcium concentrations in human blood after administration with IP6 for 20 minutes via the dialysis circuit.

Additionally, it is confirmed that IP6 chelates (sequesters) free calcium (apparatus in bypass mode) but when said apparatus is placed in dialysis mode this negative effect of chelation is overcome as the ionic calcium levels are restored as a result of the calcium supplied by the dialysis fluid (FIG. 13), thus allowing this new mode of non-bolus or prolonged release type administration via the dialysis system, which is appropriate for product efficacy, as explained in previous examples, and improves the safety profile, to be established for IP6.

Example 12

Synergistic Effect of IP6 with Other Treatments for Renal Impairment

Objective: to evaluate the potential synergies between the effects of IP6 and the effects of other treatments for renal impairment.

Experimental: hydroxyapatite (HAP) was crystallised by mixing appropriate concentrations of calcium and phosphate at pH 7.4. The effect of cinacalcet and sevelamer was simulated by suitably modifying the calcium and phosphate concentrations. The induction period (time required for HAP to begin to crystallise) was recorded as the analytical signal.

Figure 14A:
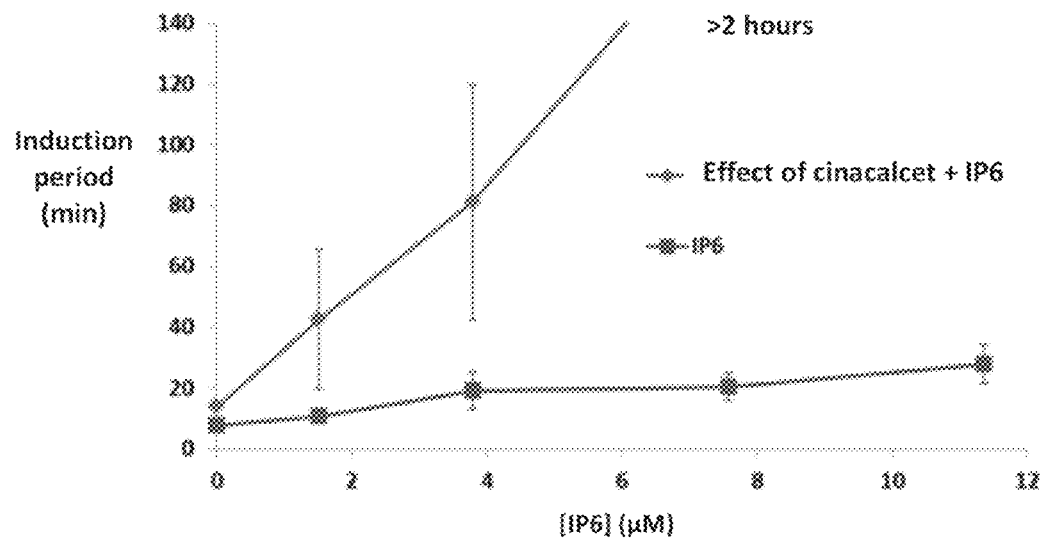
FIG. 14. Synergy between IP6 and the effect of cinacalcet (A) and sevelamer (B).
Figure 14B:
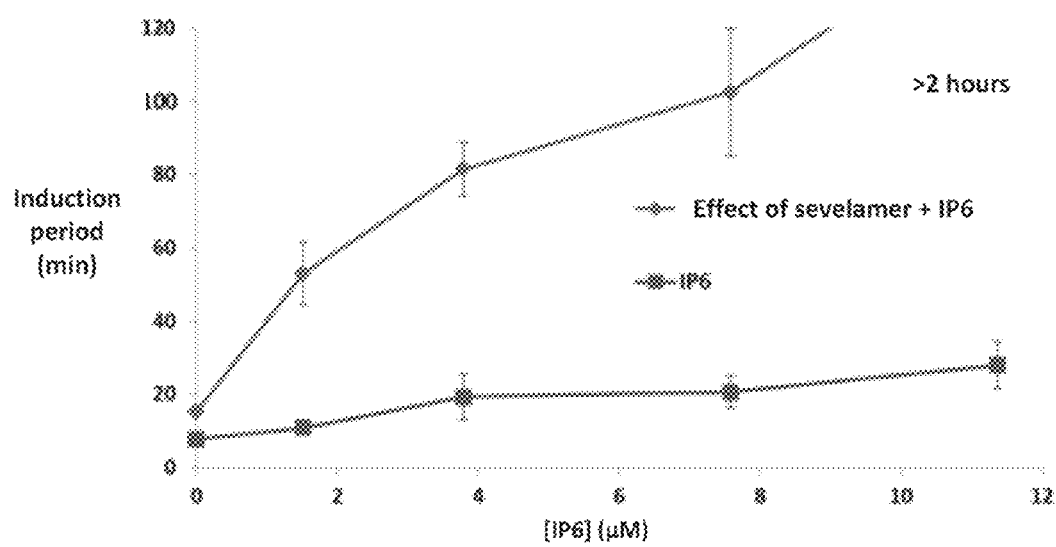

Results and discussion: the induction period for the control experiment was 8 minutes. When IP6 is added the induction time increased progressively to 28 minutes for a concentration of 11.4 µM. Subsequently, IP6 at different concentrations in the range 0-11.4 µM was combined with a constant simulated concentration of cinacalcet and sevelamer, modifying the calcium and phosphate concentrations appropriately. The induction time (without IP6) was 14 and 15 minutes, respectively, when the effect of cinacalcet and sevelamer was simulated. As can be seen from FIG. 14 a clear synergistic effect was discovered when IP6 was added.

The invention claimed is:

1. A method for the treatment and/or inhibition of a kidney failure-related disease comprising administering to a subject with kidney failure an effective amount of a medicament which comprises at least one compound of formula I, or a pharmaceutically acceptable salt thereof:

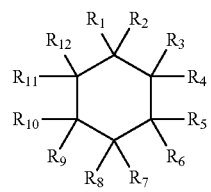

where:

$R_1$, $R_3$, $R_5$, $R_7$, $R_9$, and $R_{11}$ independently represent H or a compound of formula II:

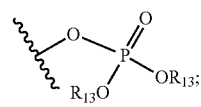

$R_{13}$ represents H;

$R_2$, $R_4$, $R_6$, $R_8$, $R_{10}$ and $R_{12}$ represent H; and wherein at least one of the radicals $R_1$, $R_3$, $R_5$, $R_7$, $R_9$ and $R_{11}$ represents a compound of formula II, characterised in that said medicament is administered in a non bolus prolonged release form, and wherein the medicament is found in a form suitable for parenteral, topical or enteral administration.

2. The method according to claim 1, where:

$R_1$, $R_3$, $R_5$, $R_7$, $R_9$ and $R_{11}$ represent a compound of formula II:

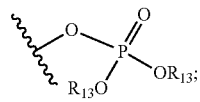

$R_{13}$ represents H; and $R_2$, $R_4$, $R_6$, $R_8$, $R_{10}$ and $R_{12}$ represent H; characterised in that said medicament is administered in a non bolus prolonged release form.

3. A method for the treatment and/or inhibition of a kidney failure-related disease comprising administering to a subject with kidney failure an effective amount of a medicament which comprises a composition comprising at least one compound of general formula I as described in claim 1 and another active substance characterised in that said medicament is administered in a non bolus prolonged release formm and wherein the medicament is found in a form suitable for parenteral, topical or enteral administration.

4. The method according to claim 3, where the active substance is selected from a list comprising a calcimimetic, vitamin, phosphorus chelator, thiosulfate, bisphosphonate, pyrophosphate, citrate, diuretic, antihypertensive and anticholesteraemic agent.

5. A method for the treatment and/or inhibition of a kidney failure-related disease comprising administering to a subject with kidney failure an effective amount of a medicament which comprises at least one compound of general formula I as described in claim 1 and a compound selected from a list comprising a calcimimetic, vitamin B, vitamin D or vitamin K, phosphorus chelator, thiosulfate, bisphosphonate, pyrophosphate, citrate, diuretic, antihypertensive and anticholesteraemic agent separately, simultaneously or sequentially, in a non bolus prolonged release form, and wherein the medicament is found in a form suitable for parenteral, topical or enteral administration.

6. The method according to claim 5, where the kidney failure-related diseases are calcium disorder-related diseases.

7. The method according to claim 5, where the calcium disorder-related diseases are selected from the list comprising renal lithiasis, cardiovascular calcification, cardiovascular disease, osteoporosis, bone cancer, podagra, calcific tendinitis, calcinosis cutis, rheumatoid arthritis, bone mineral disease, osteomalacia, adynamic bone, calciphylaxis and cardiovascular diseases.

8. The method according to claim 1, where the kidney failure-related diseases are calcium disorder-related diseases.

9. The method according to claim 1, where the calcium disorder-related diseases are selected from the list comprising renal lithiasis, cardiovascular calcification, cardiovascular disease, osteoporosis, bone cancer, podagra, calcific tendinitis, calcinosis cutis, rheumatoid arthritis, bone mineral disease, osteomalacia, adynamic bone, calciphylaxis and cardiovascular diseases.

10. The method according to claim 3, where the kidney failure-related diseases are calcium disorder-related diseases.

11. The method according to claim 10, where the calcium disorder-related diseases are selected from the list comprising renal lithiasis, cardiovascular calcification, cardiovascular disease, osteoporosis, bone cancer, podagra, calcific tendinitis, calcinosis cutis, rheumatoid arthritis, bone mineral disease, osteomalacia, adynamic bone, calciphylaxis and cardiovascular diseases.

* * * * *